United States Patent
Richman

(10) Patent No.: US 9,474,579 B2
(45) Date of Patent: *Oct. 25, 2016

(54) ORGANIZER FOR SURGICAL INSTRUMENTS AND ITEMS USED DURING SURGERY

(71) Applicant: Lawrence M. Richman, Los Angeles, CA (US)

(72) Inventor: Lawrence M. Richman, Los Angeles, CA (US)

(73) Assignee: Lawrence M. Richman, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/685,465

(22) Filed: Apr. 13, 2015

(65) Prior Publication Data

US 2016/0100890 A1    Apr. 14, 2016

Related U.S. Application Data

(63) Continuation-in-part of application No. 14/509,986, filed on Oct. 8, 2014, now Pat. No. 9,179,978.

(51) Int. Cl.
*B65D 83/10* (2006.01)
*A61B 19/02* (2006.01)

(52) U.S. Cl.
CPC ........ *A61B 19/0271* (2013.01); *A61B 50/20* (2016.02); *A61B 50/30* (2016.02);
(Continued)

(58) Field of Classification Search
CPC . A61M 5/008; A61B 19/0271; A61B 50/20; A61B 50/30; A61B 50/33; A61B 2019/0278; A61B 2019/2075; A61B 2050/3008; A61B 2050/0051; B65D 1/36
USPC ...... 206/369, 370, 373, 377, 355, 210, 571, 206/562, 563, 493, 564, 494, 477–483, 1.5, 206/459.1, 438, 366, 565, 207, 761, 765, 206/817, 804; 211/70.6, 70.7
See application file for complete search history.

(56) References Cited

U.S. PATENT DOCUMENTS 3,132,765 A     5/1964 Florendo
3,983,996 A  * 10/1976 Hendren, III ....... A61M 25/002
                                                   206/363
(Continued)

OTHER PUBLICATIONS

Amiwelisten, "Surgical Instrument counting and organizational system," YouTube, Feb. 14, 2008, https://www.youtube.com/watch?v=Oyb7i7WafAo.
(Continued)

*Primary Examiner* — Jacob K Ackun
*Assistant Examiner* — Rafael Ortiz
(74) *Attorney, Agent, or Firm* — Michael D. Harris; SoCal IP Law Group LLP

(57) ABSTRACT

An organizer for holding surgical instruments includes a tray that has instrument wells extending from the top surface of the tray. The shape of each instrument well corresponds to particular surgical instrument's shapes. Each well's depth corresponds to the height of a particular stack of surgical instruments. Pivoting locking bars extend over each instrument well to a locked position and prevent adding or removing any instruments. When the bar extends over the instrument well, it rests against the top-most instrument if the well is full. If any instruments are missing from their well, part of the locking bar projects above the tray's surface. Thus, one can notice quickly whether all instrument wells are full. The locking bar also may pivot over the instruments. The tray may have a plunger that projects about the tray's top surface if any surgical tools have not been returned to the tray.

12 Claims, 14 Drawing Sheets

(52) U.S. Cl.
CPC ...... *A61B 50/33* (2016.02); *A61B 2019/0275* (2013.01); *A61B 2019/0278* (2013.01); *A61B 2050/0051* (2016.02); *A61B 2050/3008* (2016.02)

(56) References Cited

U.S. PATENT DOCUMENTS

| | | | |
|---|---|---|---|
| 3,987,895 | A | 10/1976 | Jamshidi |
| 4,011,944 | A | 3/1977 | Cooley et al. |
| 4,046,254 | A | 9/1977 | Kramer |
| 4,153,160 | A | 5/1979 | Leigh |
| 4,767,008 | A | 8/1988 | Warnecke et al. |
| 5,170,804 | A | 12/1992 | Glassman |
| 5,294,413 | A | 3/1994 | Riihimaki et al. |
| 5,441,152 | A | 8/1995 | Estes |
| 5,505,916 | A | 4/1996 | Berry, Jr. |
| 6,230,888 | B1 | 5/2001 | Frieze et al. |
| 6,426,041 | B1 | 7/2002 | Smith |
| 7,066,328 | B2 | 6/2006 | Pulsifer |
| 7,997,847 | B2 | 8/2011 | Treat et al. |
| 8,177,064 | B2* | 5/2012 | McCormick ............... 206/370 |
| 8,627,987 | B2* | 1/2014 | Pollack ............. B65D 83/0005 220/8 |
| 2007/0095717 | A1 | 5/2007 | Tucker |
| 2010/0065456 | A1 | 3/2010 | Junk et al. |

OTHER PUBLICATIONS

Utah Medical Products, Inc. "Developmentally Friendly—Neonatal and Pediatric Intensive Care," http://www.utahmed.com/pdf/58105.pdf, Jun. 30, 2013, pp. 1-14.

Utah Medical Products, Inc. "Umbili-Cath," http://web.archive.org/web/20130630061754/http://www.utahmed.com/umbilicath.htm, Jun. 30, 2013, pp. 1-4.

World Intellectual Property Organization, International Search Report and Written Opinion for International Application No. PCT/US2015/42307, mail date Oct. 29, 2015, pp. 1-14.

\* cited by examiner

ORGANIZER FOR SURGICAL INSTRUMENTS AND ITEMS USED DURING SURGERY

RELATED APPLICATIONS

This application is a continuation-in-part of application Ser. No. 14/509,986, filed Oct. 8, 2014, by Leo Gordon, et al., "Organizer for Surgical Tools and Items Used during Surgery." Applicants claim priority based upon that application.

BACKGROUND

1. Field

Organizers for holding surgical instruments in operating rooms.

2. General Background and State of the Art

Surgeons and their staff need their instrument and other items used during surgery to be readily accessible and well organized. Spending time looking for a clamp that other instruments hide adds crucial time to a surgery. That is undesirable for the patient because delays increase the length of the surgery and time under anesthesia.

Increasing the time for each surgery also is detrimental to surgeons, accompanying physicians and staff and to the hospital or surgical center. Surgeons and other physicians and staff are in high demand and often perform many procedures daily. Adding time to each surgery can eliminate one or more surgeries per day or force a surgery planned for one day to be delayed to the next or a later day.

For hospitals and surgical center, delays for each surgical team are compounded. The operating rooms at many hospitals are fully utilized. That fact alone causes delays in scheduling patients' surgeries. In addition, if some or all the operating rooms handle even one fewer procedures every day, the hospital becomes less efficient. Therefore, costs increase. Because fully equipped operating rooms are very expensive, adding more operating rooms is costly. On the other hand, having any added but under-utilized operating rooms generates less revenue to pay for the operating rooms or for other hospital expenses.

Increased costs and decreased efficiency are not the only concerns. At the end of each procedure, all instruments must be accounted for. For example, if the surgeon starts with 15 surgical clamps and has five unused surgical clamps left at the end of the surgery, the other ten must be accounted for. Otherwise, a missing clamp might be inside the patient. More likely, it may be hidden on the operating table or dropped on the floor. Finding the clamps may not be difficult and may not take excessive time, but the time spent adds up for each operating room, each hospital and hospitals in general.

SUMMARY

An organizer for holding surgical instruments includes a tray that has indentations extending down from the top surface of the tray. The indentations form instrument wells. Each instrument well has a shape that corresponds to the shape of particular surgical instruments. For example, the instrument well for a scissors has two round regions to receive the scissors' finger openings, a rectangular region extending from the round regions and a narrow region corresponding to the scissors' pointed end. Likewise, the instrument well for scalpels has a tapered length corresponding to the handle and a narrower region for the blade.

The depth of each instrument well corresponds to the height of a stack of the surgical instruments that a surgeon plans to use. For example, if a particular surgery typically uses three scalpels, the depth of the scalpel instrument well would accommodate the three scalpels. If another type of surgery uses more than three scalpels, the instrument well would be deeper. Otherwise, more than one instrument well could be used with the scalpels divided between the wells.

The tops of the stack may be aligned with the tray's top surface or the stacks should be the same, short distance below that surface. After surgery, the used instruments are returned to their instrument well. Thus, at a glance, one can tell whether the instrument well is full. If any instrument wells are not full, an instrument is missing and must be found.

The tray may have locking bars at the top or upper surface of the tray, which extend over each instrument well. In that position, instruments cannot be added to or removed from the instrument well. The bar can pivot or otherwise move to a position uncovering the instrument well so that instruments can be the removed and added to the instrument well. When the bar extends over the instrument well, the bar will be against the top instrument in the instrument well if the well is full. Seeing that contact between the bar and the top instrument allows one to see immediately whether the instrument well is full. In the event that a surgical instrument is missing, the far end of the locking bar may be offset to project upwards to alert the operating staff of the missing instrument.

If the instruments are returned to their instrument well following surgery, each instrument well should contain the same number of instruments that filled the instrument well when the surgery started. If one or more instruments are missing from their instrument well, the locking bar's intersection with the structure of the tray adjacent the instrument well is such that an end of the locking bar projects about the tray's surface. Thus, one can notice quickly whether all instrument wells are full because all surgical instruments are returned to their indentation.

To assist the operating room staff further, part or all of the top of the locking bar may be colored green or another color so that when the locking bar in the closed position over the instruments, the surgeon or staff member can see that the bar is closed. Similarly, part or all of the opposite side of the locking bar may be colored red or another color different from the first side of the locking bar. Therefore, one will see red when the locking bare is in the open position when instruments are being used. At the end of the operation, the operating room staff can be assured that all instruments are accounted for when all the locking bars are fully flush with the tray and show green over each instrument well. Instead of color, the top and bottom of the locking bar may have contrasting symbols.

The locking bar's fulcrum may be positioned so that part of the bar sticks up if the instrument well is not full.

Alternatively, the tray could contain a locking plate that pivots about an axis perpendicular to the tray's top surface. In an unlocked orientation, the locking plate is out of the way of the surgical instruments in the instrument well. Pivoting the locking plate about its axis moves part of the locking plate over the top-most surgical instrument to lock the instruments in the instrument well.

A spring can mount below the bottom-most instrument to urge the instruments upward toward or above the tray's top surface. A plunger may be mounted adjacent the instrument well. A base extending from an upright portion of the plunger extends under the bottom-most instrument in the instrument well, and the spring mounts below the base of the plunger. When at least one instrument is removed from the well, the spring urges the plunger upward such that the top of the upright portion of the plunger extends above the top of the tray. After surgery and after all the instrument are returned to their respective instrument wells, one can determine if any instruments are missing because the tope of at least one plunger extends about the tray's top surface.

DETAILED DESCRIPTION

Figure 1:
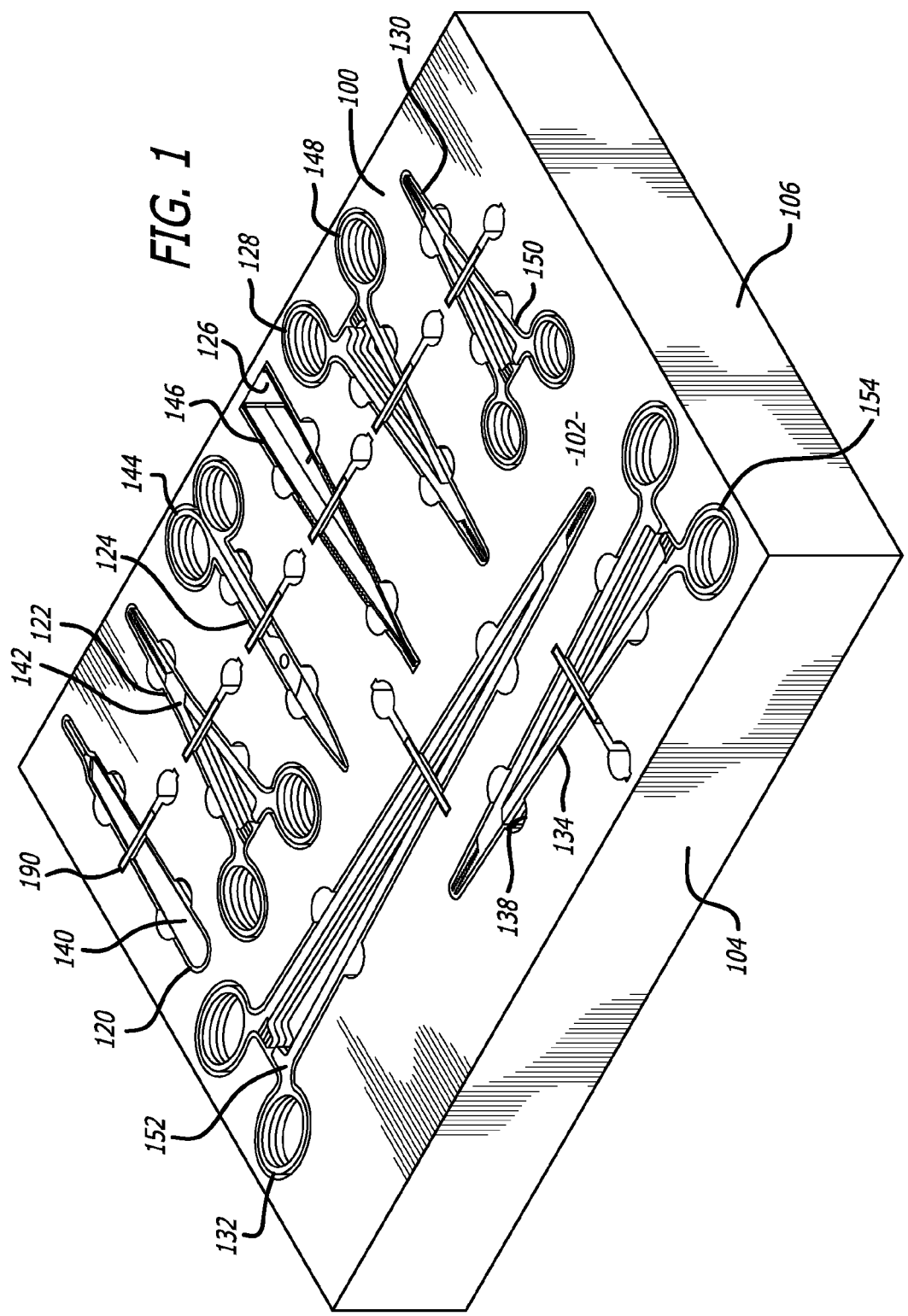
FIG. 1 is a perspective view one version of the tray showing instruments in the instrument wells.

Tray 100 (FIGS. 1, 2 and 3) for holding surgical instruments may be made from any suitable material such as plastic or non-corrosive metal such as stainless steel, but cardboard, formed paper and composites are options. The nonmetal materials may be easier to form and are less costly than metal. The material for the tray shown in the drawings is rigid, but the material could be bendable.

Tray 100 may be disposable. However, non-disposable materials should be able to retain their form when subjected to autoclave temperatures (100° C. at 20 psi) or whatever temperatures and pressures are customary for a particular facility.

Tray 100 shown in the drawings has a top surface 102 and depending sidewalls, only three of the four, 104, 106 and 108, are visible in the drawings. The tray is rectangular, but other shapes such as polygons, circles, ellipses and other freeform shapes could be acceptable.

Figure 3:
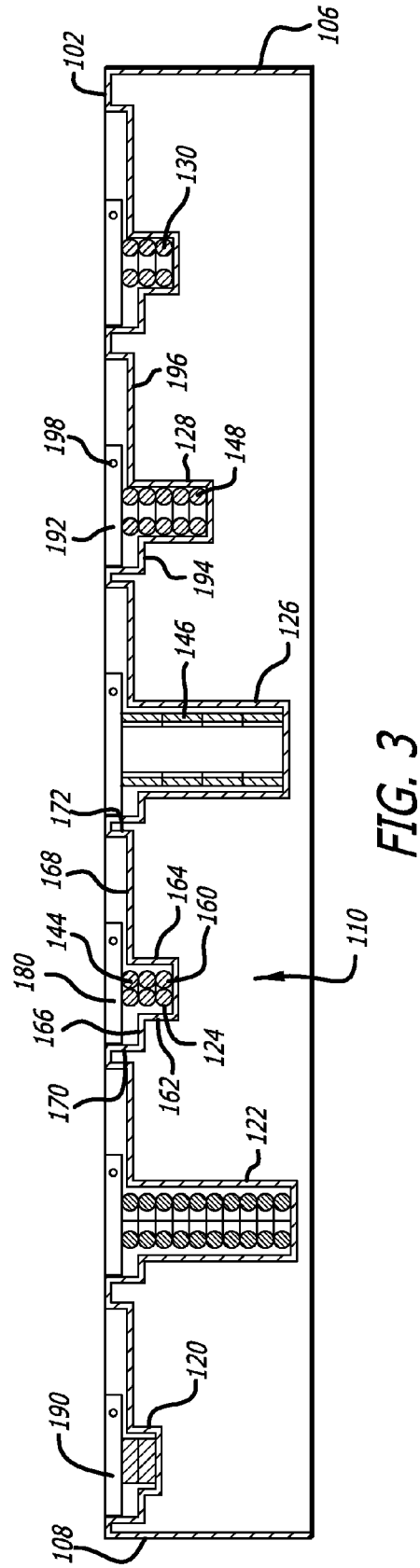
FIG. 3 is a side, sectional view one version of the tray taken through plane 3-3 of FIG. 2.

The base of tray 100 is open, but it could be closed. With the base open, one has access to the tray's underside 110 (FIG. 3).

Top surface 102 of tray 100 has several indentations that form instrument wells for receiving surgical instruments.

Eight instrument wells, 120, 122, 124, 126, 128, 130, 132 and 134, are shown in the drawings, but the tray could have more or fewer instrument wells. Rather than adding many instrument wells to make a tray that may be too large, two or more trays of a desired size could replace a single, large tray.

Figure 2:
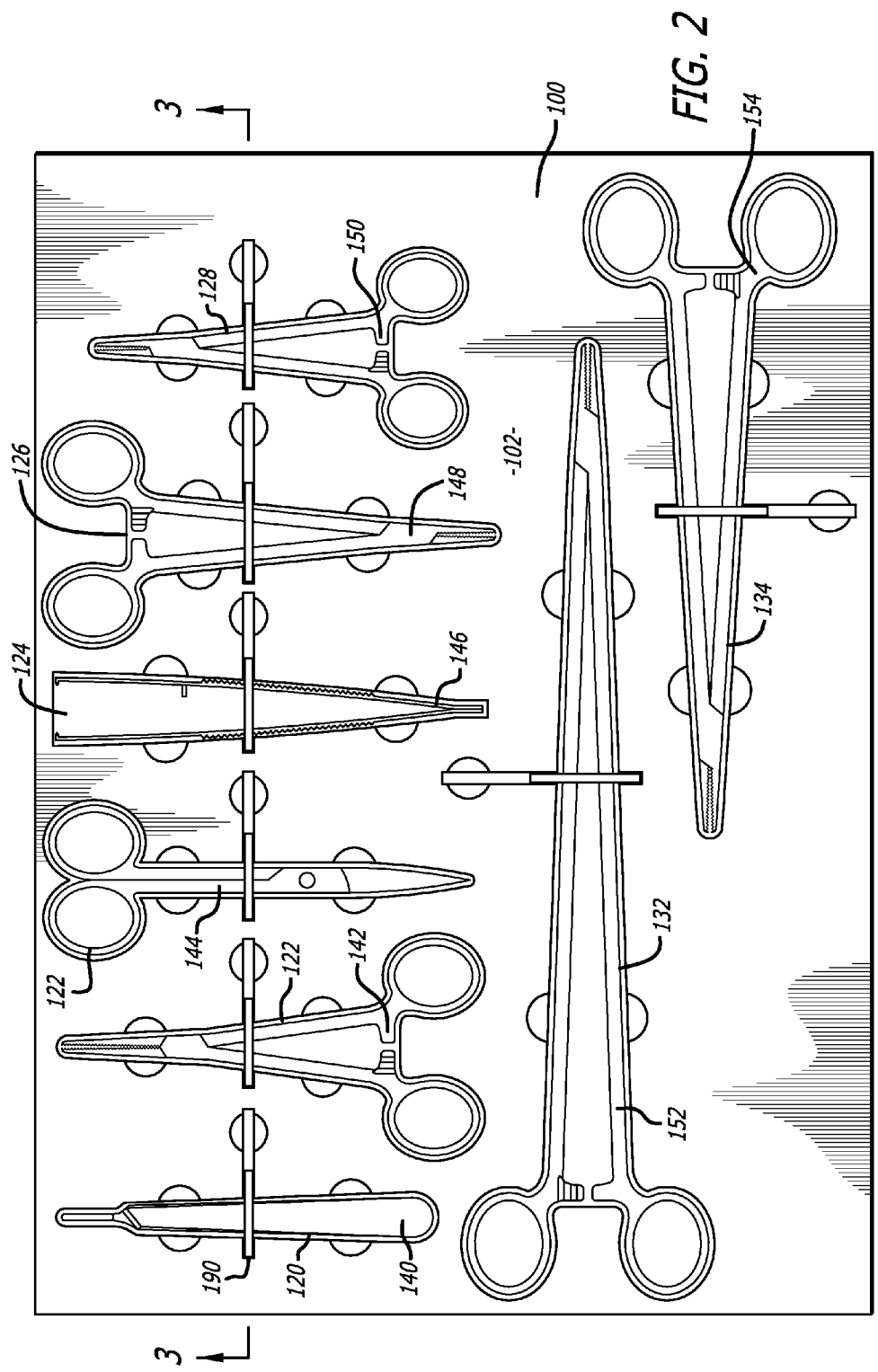
FIG. 2 is a plan view one version of the tray showing instruments in the instrument wells.

Each instrument well is shaped to receive a particular instrument. For example, well 120 is shaped to receive scalpels 140 (FIGS. 1 and 2). Instrument wells 122 receives surgical clamps 142. Scissors 144 fit into instrument well 144, and forceps 146 fit into instrument well 126. Well 128 holds more clamps 148. Small, medium and large needle holders 150, 154 and 152 are received in wells 130, 134 and 132, respectively. The instrument wells may have depressions 138 at appropriate places to allow easier gripping of an instrument.

FIG. 3 shows that the instrument well may have different depths to accommodate different sizes and numbers of surgical instruments. For example, consider instrument well 124 in FIG. 3, which receives scissors 144. The indentation that forms the instrument well includes base 160, which depends from sidewalls 162 and 164. The tops of the sidewalls intersect shoulders 166 and 168, and the outside of each shoulder intersects short extension 170 and 172. The extensions intersect top surface 102 of tray 100. The functions for the space above the shoulders are discussed below.

Experienced surgeons anticipate that they will use a specific number of each surgical instrument for a specific surgery. Accordingly, the number of instrument wells and their shapes for particular instruments could vary for specific surgeries.

Consider a surgeon who anticipates for a particular procedure needing three scissors of the size of scissors 144 in FIG. 1. Thus, for that surgery, the instrument well is deep enough to hold three scissors—no more and no fewer. Similarly, if the surgeon anticipates needing four forceps, instrument well 126 is deep enough to hold four forceps 146. Because the forceps are thicker than the thickness of scissors 144, the instrument well 126 holding four forceps is much deeper than the instrument well 124 holding three scissors. The deepest instrument well, 122, holds ten surgical clamps 142.

A leaf or other spring (not shown) could be used at the bottom of some or all the instrument wells to urge the instruments upward. Such an arrangement could assist in gripping the top-most instrument.

Figure 4:
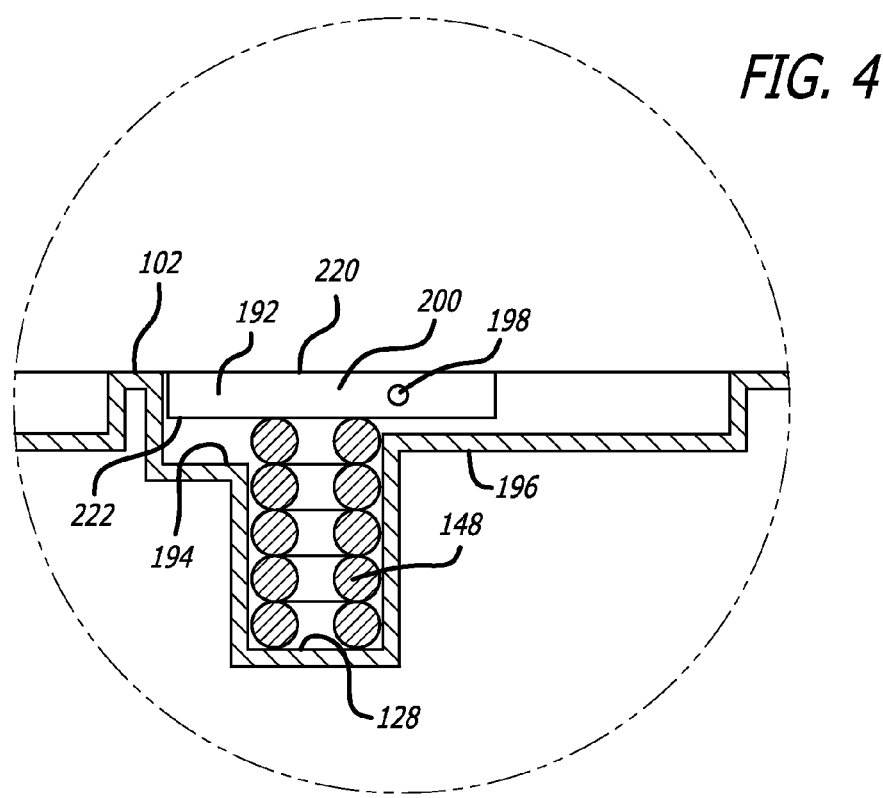
FIGS. 4 and 5 are sectional views of one instrument well at the tray's top surface.

A locking bar extends over the top-most instrument in each instrument well. The locking bars are similar; only locking bars 190 and 192 are discussed. Instrument well 128 holds five forceps or surgical clamps 148 (FIG. 4). Locking bar 192 mounts on pin 198 in the space above shoulders 194 and 196. The locking bar's top face 200 is in the same plane as top surface 102 of tray 100. The locking bar is seen resting on the upper-most forceps in FIG. 4.

Figure 6:
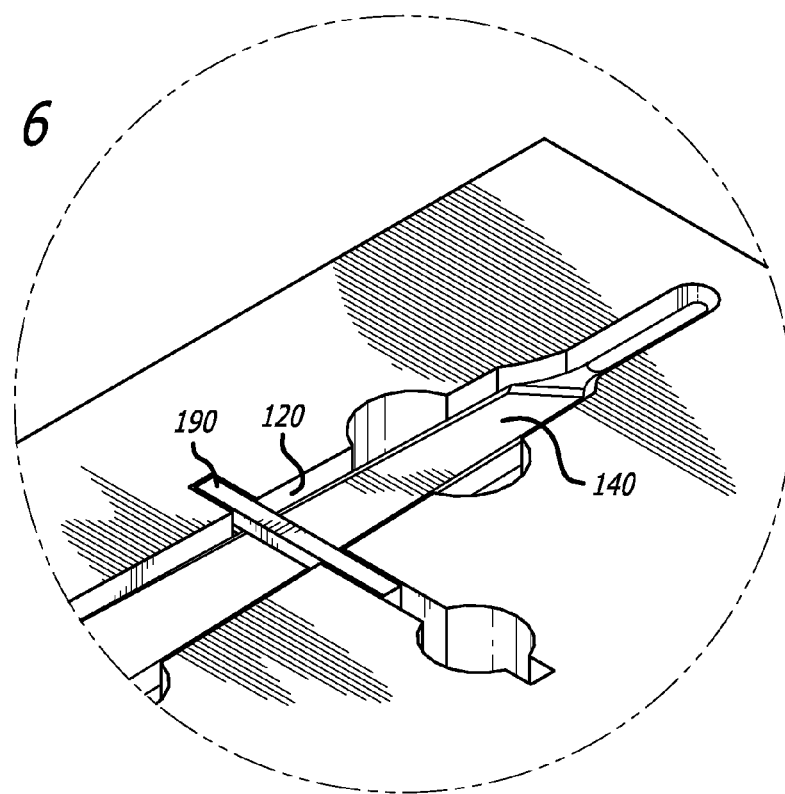
FIGS. 6, 7, 8 and 9 are perspective views of one instrument well at the tray's top surface showing the locking bar in different orientations.
Figure 7:
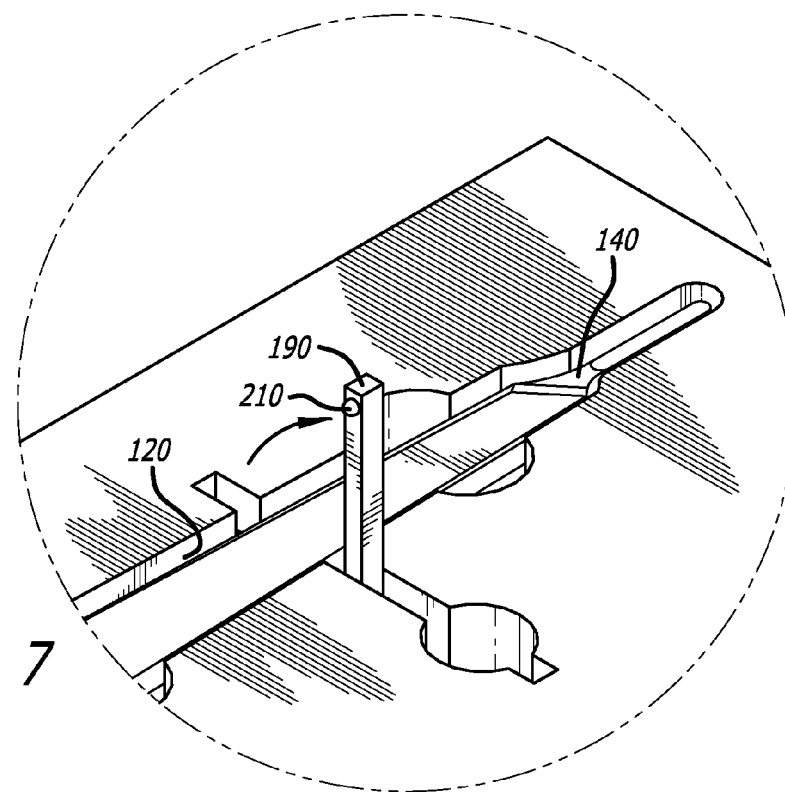
Figure 8:
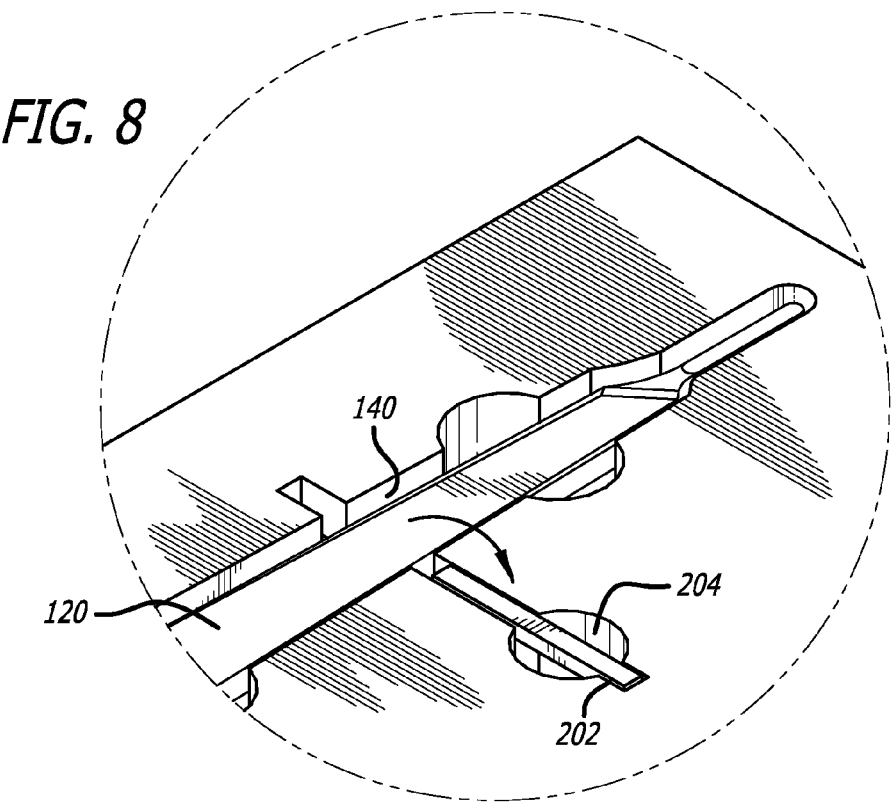

To remove an instrument from an instrument well, the locking bar is pivoted to or past vertical. Thus, as FIGS. 6 and 7 show, locking bar 190 pivots about its pin (not shown) from the horizontal position over instrument well 120 and scalpels 140 (FIG. 6) to a vertical orientation (FIG. 7). The locking bar can continue to rotate to the FIG. 8 position where it rests in groove 202. In that position (and it the FIG. 6 position), a person moving his or her hand over the top 102 of tray 100 will not encounter any obstructions. The groove also may have depressions 204 that allow insertion of a finger or tool to pull the locking bar out of the groove. The locking bars may have a spring-loaded pin 210 that engages a detent (not shown) in the groove. That arrangement tends to hold the locking bar over the instruments until one rotates the locking bar away from the instruments.

Figure 5:
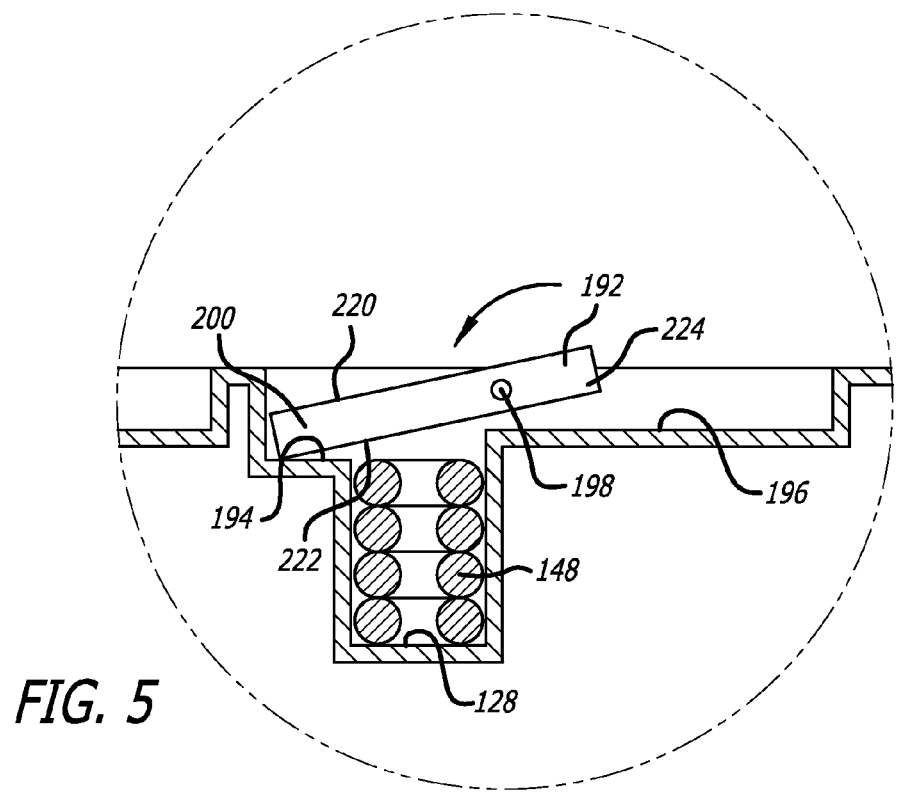

The locking bar may have different colors on its top and bottom. All or part of top face 220 (FIG. 4) could be colored green, for example, which would show that all locking bars are in their locked or almost locked (FIG. 5) position. All or part of bottom face could be colored red, for example, so that the red face would show when the locking bar is open to allow access to instrument well 148. Symbols could replace the colors.

In the drawings, the locking bars pivot over and away from the instrument wells. Other arrangements are possible although they may not offer all the advantages of the pivoting locking bars. For example, the locking bar could slide in an elongated groove from a position over the instrument well to a position spaced from the instrument well. Likewise, a U-shaped fastener could be inserted into openings adjacent the sides of each instrument well. Other arrangements also are possible.

When the surgery begins, the surgeon or assistant opens all the locking bars, e.g., bars 190 and 200, of fully loaded tray 100. Of course, not all locking bars must be opened in the beginning, but doing so may be more convenient. As the surgery proceeds, the surgeon and his or her staff use the instruments as necessary until the surgery is finished. Then the instruments are returned to their original instrument well.

When all five forceps or surgical clamps 148 are returned to instrument well 128 and locking bar 200 is pivoted to its lock position, the locking bar aligns with the top surface 102 of tray 100. See FIG. 4. However, if only four clamps are returned to their instrument well, when the locking bar is pivoted to the lock position, the end of the locking bar continues until it contacts shoulder 194. See FIG. 5. The right side of the locking bar (FIG. 5) projects above the top surface of the tray. That is because pin 198, which acts as a fulcrum is closer to the short side 224 of the locking bar. Thus, one knows at a glance or by running a hand over the tray that at least one forceps is missing from its instrument well.

Figure 9:
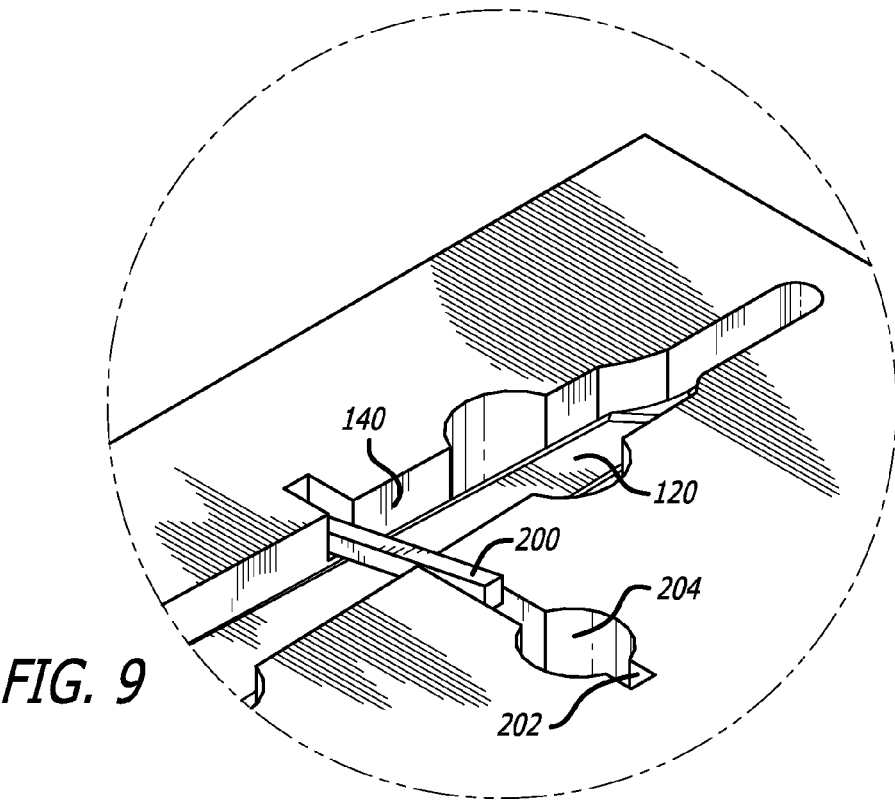

Likewise, if fewer than two scalpels 140 are returned to instrument well 120, locking bar 200 will not be flat. See FIG. 9. One can easily tell that at least one scalpel is missing.

Thus, one advantage of having pivoting locking bars such as bars 190 or 200 is their orientation projecting above surface 102 of tray 100 when the instrument well is not full. Upon finding a tool missing from the tray, those in the operating room can search for the tool. Because the search is part of the time spent returning the instruments to the tray, locating all the instruments used is handled at one time and becomes more efficient.

Figure 10:
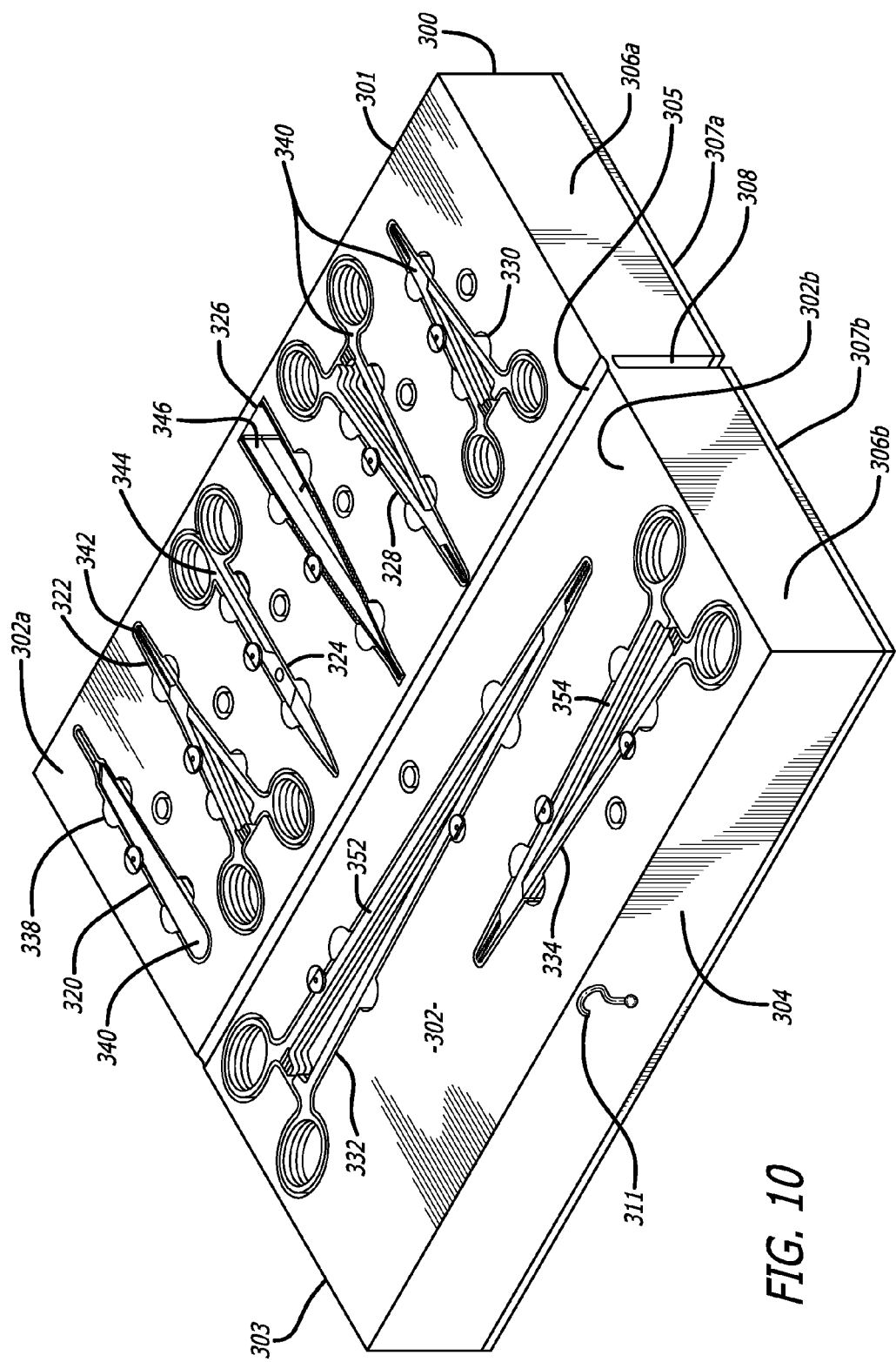
FIG. 10 is a perspective view a second version of the tray showing instruments in the instrument wells.
Figure 11:
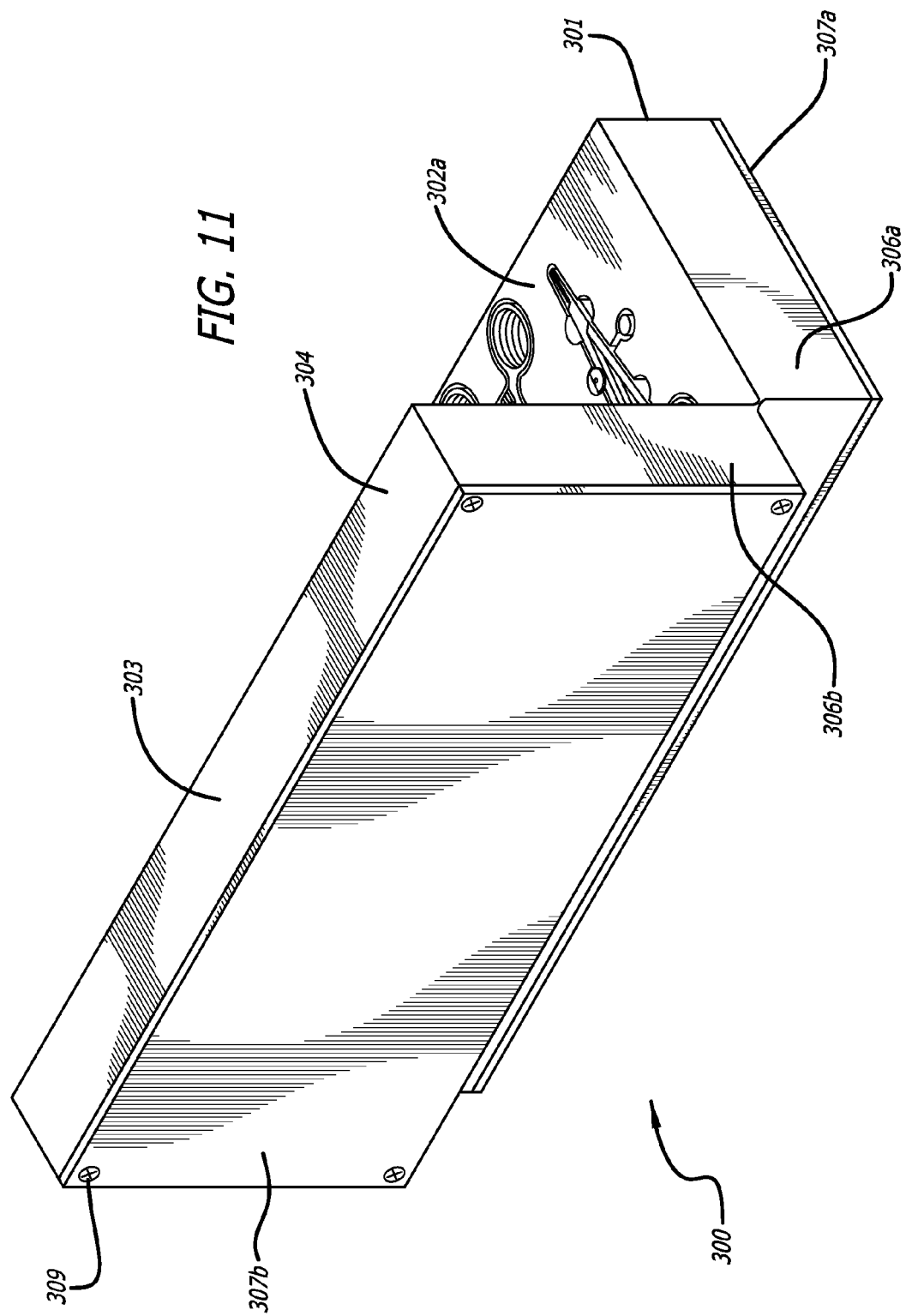
FIG. 11 is a perspective view the second version of the tray showing part of the tray folded relative to another part of the tray.
Figure 12:
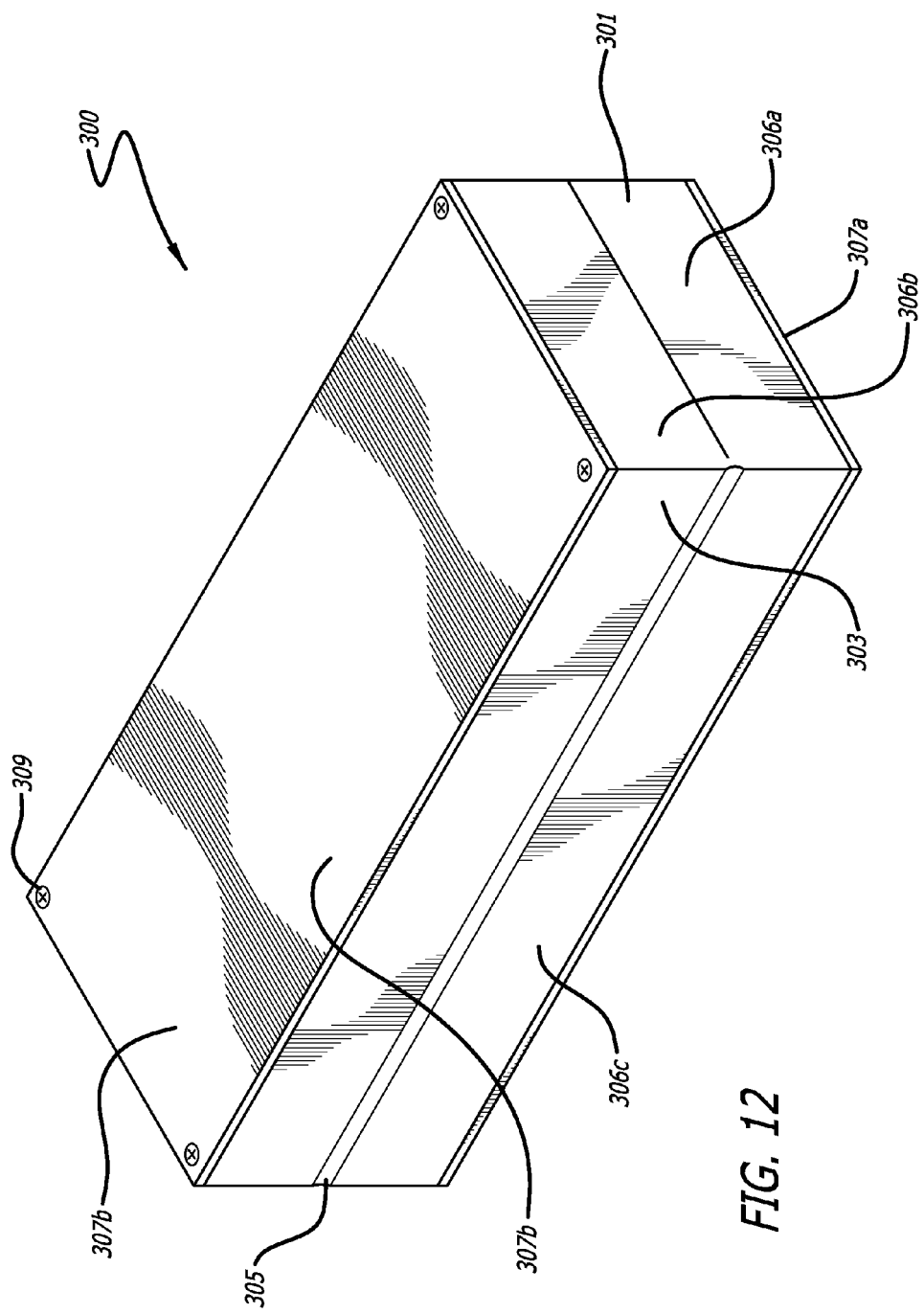
FIG. 12 is a perspective view the second version of the tray showing part of the tray fully folded relative to another part of the tray.

A second version of the organizer includes tray 300 (FIGS. 10, 11 and 12). The material for the tray is similar to the materials of tray 100 (FIG. 1). The material for the tray shown in the drawings is rigid, but the material could be bendable.

Tray 300 may be divided in at least two sections 301 and 303. The two sections that FIGS. 1 through 3 show may be hinged at 305 together to allow one section to fold over the other. Compare FIG. 1 with FIGS. 2 and 3, in which FIG. 1 is open, FIG. 3 is closed and FIG. 2 is between open and closed. The tray may have structure for securing the two sections in the closed position. For example, hook 311 (FIG. 10) on section 303 can engage a pin, eye or other structure (not shown) on section 301.

If the tray is plastic, hinge 305 could be a plastic living hinge. This type of hinge is formed during injection molding. Fabric, metal or plastic or other types of hinges could be used instead of a living hinge.

Tray 300 may be disposable. However, any non-disposable materials should be able to retain their form when subjected to autoclave temperatures.

Tray 300 shown in the drawings includes a top surface 302 that is divided into surface regions 302a and 302b. The tray is rectangular, but other shapes could be acceptable. The tray also has depending sidewalls, only three of which, 304, 306a and 306b, are visible in FIG. 10. See also sidewall 306c (FIG. 12). The two sections 301 and 303 may be spaced apart along gap 308 when the tray is in its open (FIG. 10) configuration.

Figure 14:
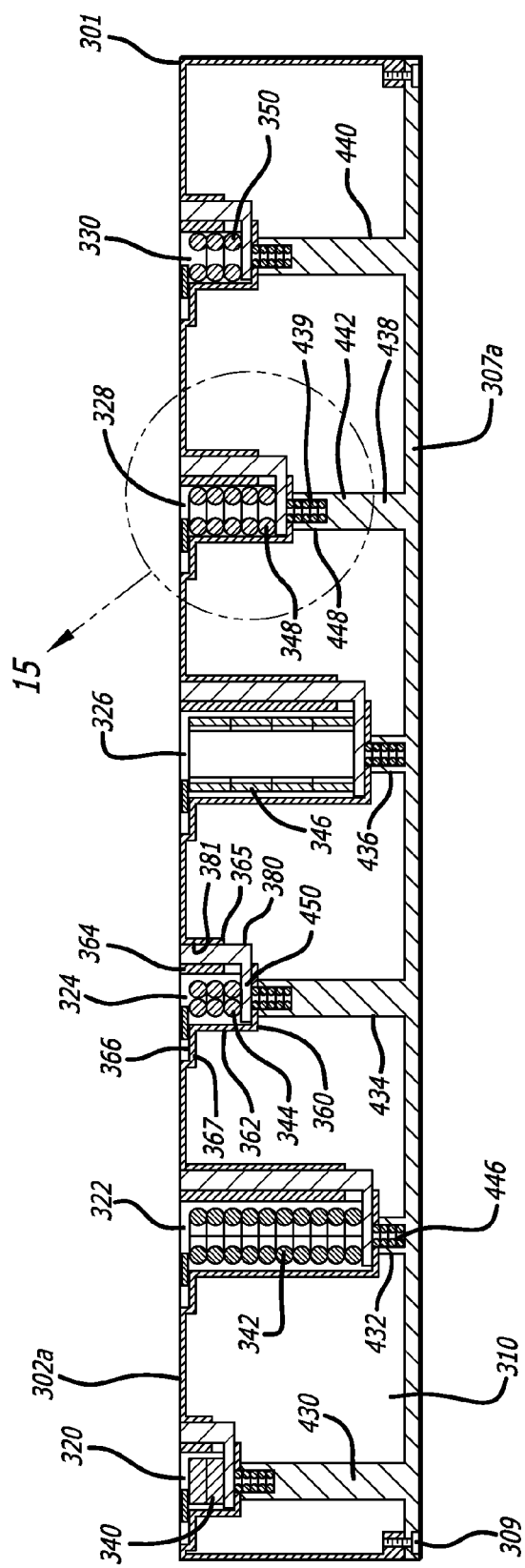
FIG. 14 is a side, sectional view the second version of the tray taken through plane 14-14 of FIG. 13.

The base of tray 300 may be open, but the base is closed in this version. That is, plates 307a and 307b cover the base. (FIGS. 10, 11, 12 and 14). The plates may be removable. Therefore, the plates are fastened with screws 309 or other fasteners to the base of the tray. Removing the plates allows access to the tray's inside 310 (FIG. 14).

Indentations in top surface 302 of tray 300 form instrument wells that receive surgical instruments. The drawings show eight instrument wells, 320, 322, 324, 326, 328, 330, 332 and 334, but the tray could have more or fewer instrument wells.

Positioning the surgical instruments on one side or the other of surface 302 facilitates opening and closing of the tray. See FIGS. 10 and 13, which show no instrument extending past hinge 305. Note that the axis of each instrument wells is perpendicular to the hinge, but angling one or more of the instrument wells could accommodate longer instruments. Likewise, orienting the instrument wells differently may allow the tray to hold more instruments.

Figure 13:
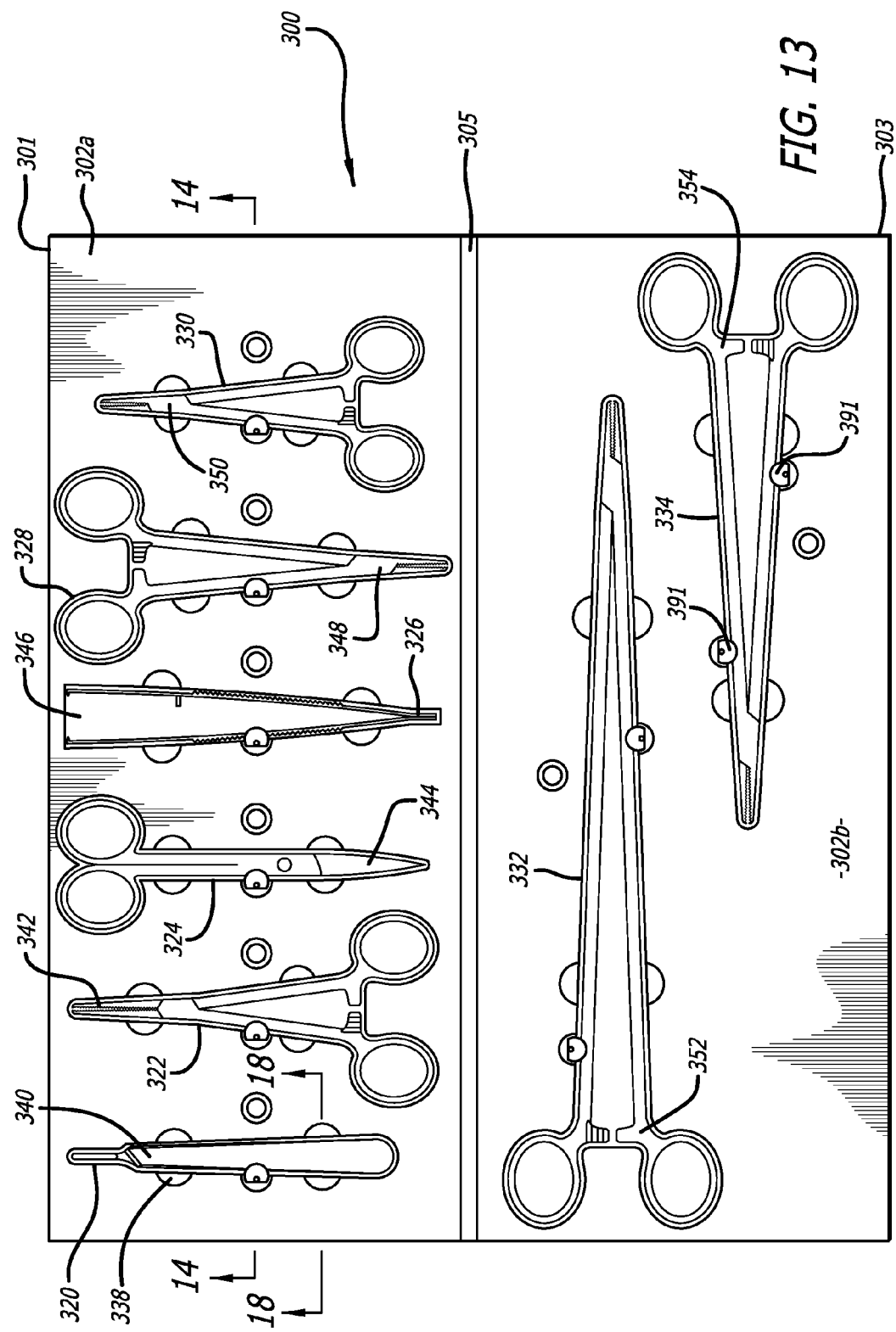
FIG. 13 is a plan view the second version of the tray in its "open" configuration. The drawing shows instruments in the instrument wells.

The shape of each instrument well conforms to that of a particular instrument. For example, well 320 is shaped to receive scalpels 340 (FIGS. 10 and 13). Instrument well 322 receives surgical clamps 342. Scissors 344 fit into instrument well 344, and forceps 346 fit into instrument well 326. Well 328 holds additional clamps 348. Instrument wells 330, 334 and 332 receive small, medium and large needle holders 350, 354 and 352, respectively. The instrument wells may have depressions such as depression 338 at appropriate places to allow easier gripping of an instrument by one's fingers or with a tool. See FIGS. 10, 13, 18, 19 and 20.

The instrument wells may have different depths to accommodate different numbers of surgical instruments and instruments of different dimensions. For example, consider instrument well 324 in FIG. 14's sectional view. That well receives scissors 344. The indentation that forms the instrument well includes bottom 360, which is at the bottoms of sidewalls 362 and 364. The top of the sidewall 362 intersect shoulder 366, which extends into a short extension 367, which intersects top surface 302a. Sidewall 364 extends to top surface 302a.

Bases 307a and 307b have pillars extending upward from the base to support the respective instrument wells. The drawings only show the pillars for base 307a. See FIG. 14, which show pillars 430, 432, 434, 436, 438 and 440. Each pillar 430, 434, 438 and 440 has a pedestal section with a cavity on top. See cavity 439 on pedestal 442 in FIGS. 14, 15, 16 and 17. Because instrument well 322 is deeper than other wells and extends almost to base 307a, pillar 432 needs no pedestal section to raise its cavity 433 high enough for its surgical instruments to reach near surface 302a. Thus, its cavity extends to base 307a. Because the pillars, pedestals and cavities perform similar functions, only the structure for pillars 432 and 438 are discuss further in detail.

Each cavity contains a coil spring. See spring 448 in FIGS. 14, 15, 16 and 17 and spring 446 in FIG. 14. Leaf springs or other types of resilient structure could substitute for coil springs. In the drawings, the cavities may be cylindrical to receive round coil springs. If other types of springs are used, the cavities can be sized to contain the springs. If so, the pillars may be sized to accommodate different sizes and shapes for the cavities.

Springs such as springs 446 and 448 extend through the base of their respective instrument well, e.g., bottom 360 of well 324. The spring urges arm 450 of plunger 380 upward. Likewise, spring 448 extends through an opening in base 449, where it urges arm 456 of plunger 452 upward. The upward force from each spring urges the surgical instrument within the respective instrument well upward toward top surface 302a or 302b.

Plunger 380 mounts in opening 381. See FIGS. 10, 13 and 14. Corresponding plungers mount next to each of the other instrument wells. Plunger 380 (FIG. 14) includes upright portion 382 and base 384 at the bottom of the upright portion. The base of the plunger extends into instrument well 324 below the surgical instrument, scissor 344, which is the instrument in instrument well 324.

Plunger 452 for instrument well 328 is shown in more detail in FIGS. 15, 16, 17 and 18. The plunger includes upright portion 454 and base 452. The plunger's base extends below surgical clamps 348, which are in instrument well 324. When instrument well 328 is full, i.e., containing five surgical clamps, locking plate 390 hold the clamps in place against the upward force from spring 448. The locking plates are described below.

Assume that during a surgical procedure, a surgeon plans to use fifteen surgical clamps of the size of clamps 342 and 348 (FIGS. 14, 15, 16 and 17). Ten clamps 342 are in well 322. Thus, for that surgery, the other instrument well, well 328m should be deep enough to hold five clamps—no more and no fewer. Though the version shown in FIG. 14 divides the clamps ten in one well 322 and five in the other well 328, the depth of each well could have a total depth to receive fifteen clamps divided nine and six, eight and six or some other division. Similarly, if the surgeon anticipates needing four forceps, instrument well 326 is deep enough to hold four forceps 346. Because the height of the forceps are greater than the clamps' height, instrument well 326, which holds four forceps, is deeper than the instrument well 328 holding three scissors. The deepest instrument well, 322, holds ten surgical clamps 348.

The instrument wells could be made deeper to accommodate additional surgical instruments, but when the normal number of instruments is used with the deeper well, a spacer could be installed below the instruments so that the top-most instrument is in a position similar to that of the top-most instrument in FIG. 14.

A locking bar or plate extends over the top-most instrument in each instrument well. The locking plates for all wells are similar; only locking plate 390 (FIGS. 15-18) is discussed. Instrument well 328 holds five surgical clamps 348 (FIG. 4). Locking plate 390 mounts on shaft 392, which extends into shoulder 366. The locking plate's top face 400 is in the same plane or close to the same plane as the tray's top surface 302a. The locking plate is in its locked position on the upper-most clamp of the five clamps in FIG. 15. The locking plates can be semicircular. By having the curved or semicircular surfaces of all locking plates in their locked orientation, one can look at the tray and determine if all locking plates are in their locked position. See FIG. 15 in which the curved side of each locking bar on half 301 faces to the right. Having more than one locking bar for larger instruments such as medium and large needle holders 354 and 352 may be desirable. Thus, two locking plates 391 lock those instruments. The circular surfaces also face each other. In addition to the viewing advantage provided by semicircular locking plates, the circular outer surface of the locking plates slides more easily over the top-most surgical instrument when the plates are pivoted to their locked position.

The locking plates could have a stop or stops (not shown) such that when each locking plate reaches the locked or unlocked position, the locking plate stops in that position. A stop also could provide touch feedback whether the locking plate is locked or unlocked. The locking plates also may have indicia such as an arrow or other distinct figure. Similarly, the opposite sides of the lacking plates could have contrasting colors. The indicia or contrasting colors make determining if all locking plates are locked easier.

Figure 15:
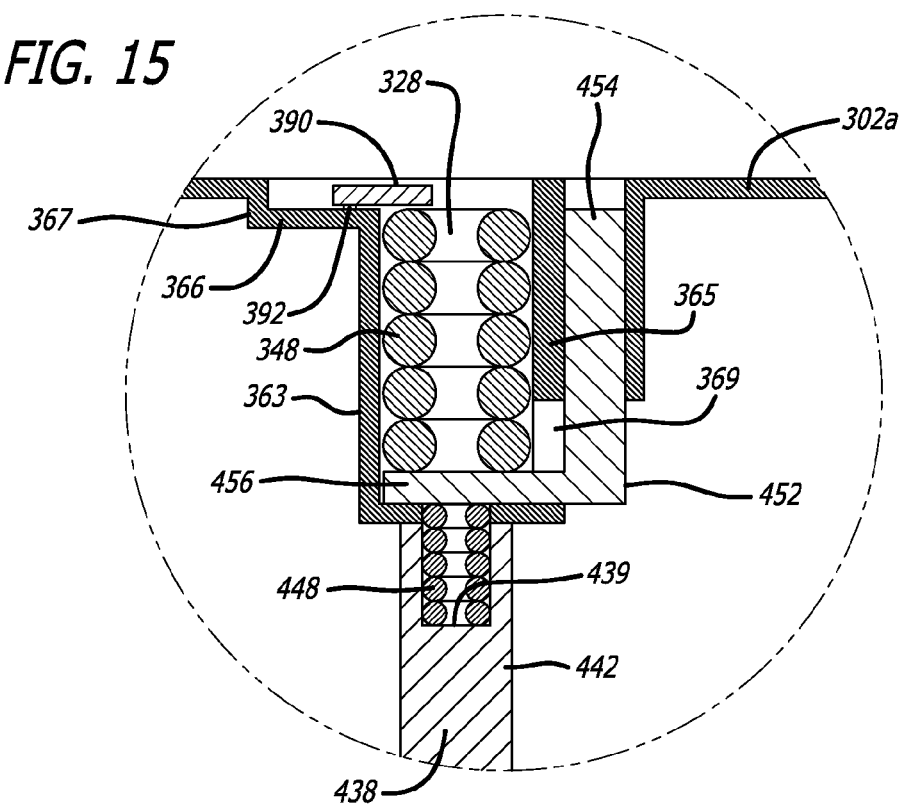
FIGS. 15, 16 and 17 are sectional views of a portion of an instrument well showing detail 15 in FIG. 14.
Figure 16:
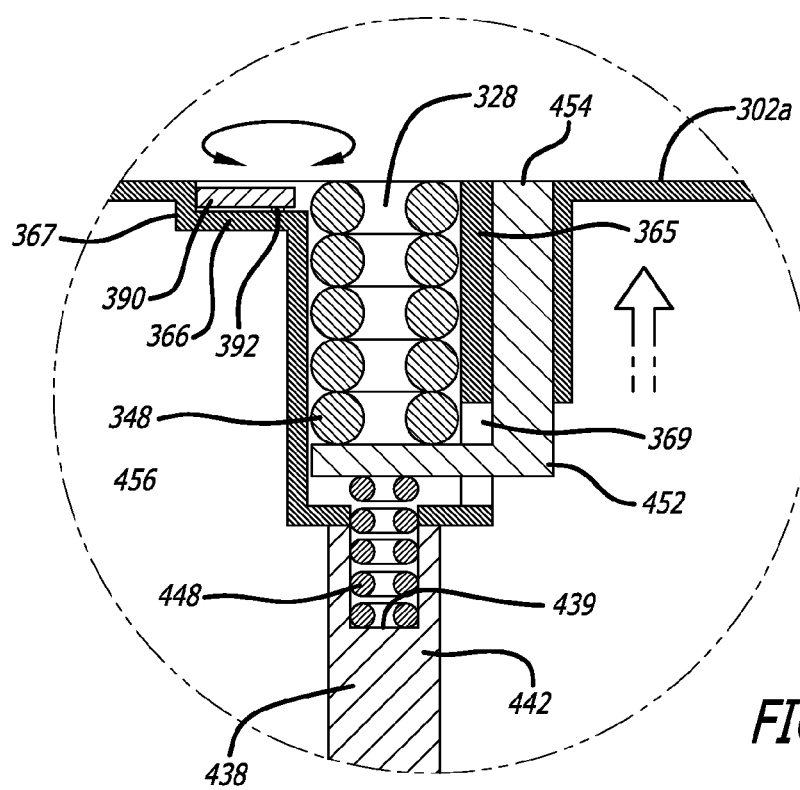

When a person wants to remove an instrument from an instrument well, he or she rotates locking plate 390 from the FIG. 15 position to the FIG. 16 position. See also FIGS. 19 and 20, which show locking plate 394 interacting with scalpels 340 in instrument well 320. When the locking plate is in the FIG. 19 position, it is over a portion of the uppermost scalpel 340 and blocks removal of the instrument from instrument well 320. In the FIG. 20 position, the locking plate pivots out of contact with the scalpel, which allows removal of the scalpels.

When the two halves 301 and 303 of the tray are moving between their open and closed positions, locking plates e.g., plate 394, prevent the surgical instruments from falling out of the instrument wells.

Before surgery begins, the instrument wells are loaded with the correct number of the proper instruments, and all locking plates are rotated to the locked orientation. Therefore, each instrument is secured in its respective instrument well. The surgeon or assistant opens all the locking plates, e.g., plate 390, of fully loaded tray 300. Of course, not all locking plates must be opened in the beginning, but doing so may be more convenient.

Figure 17:
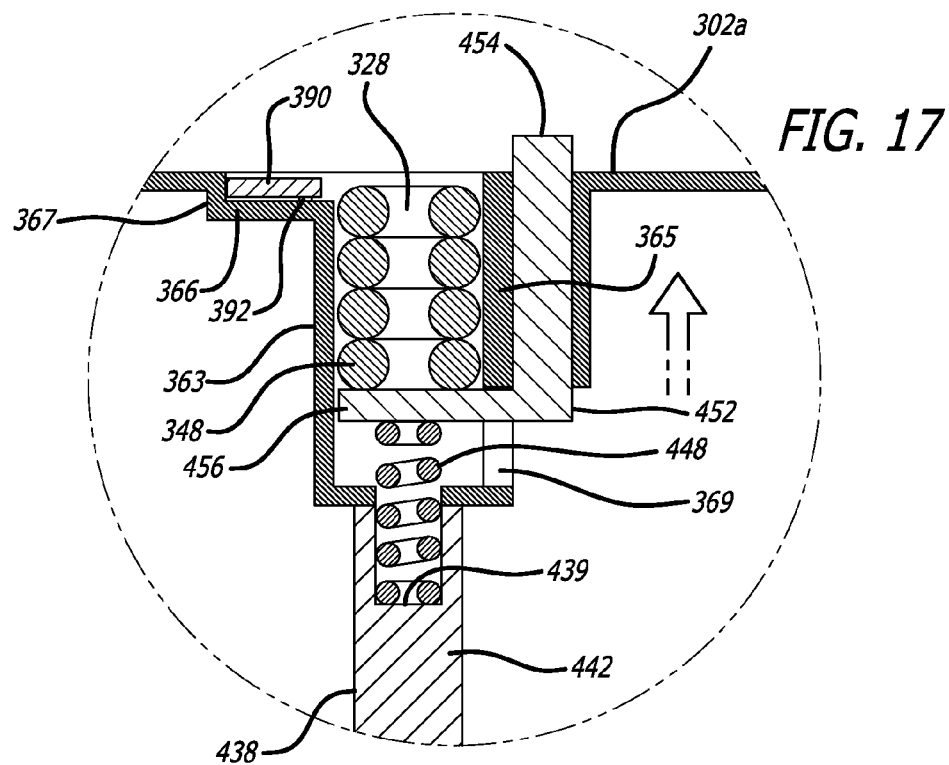
Figure 18:
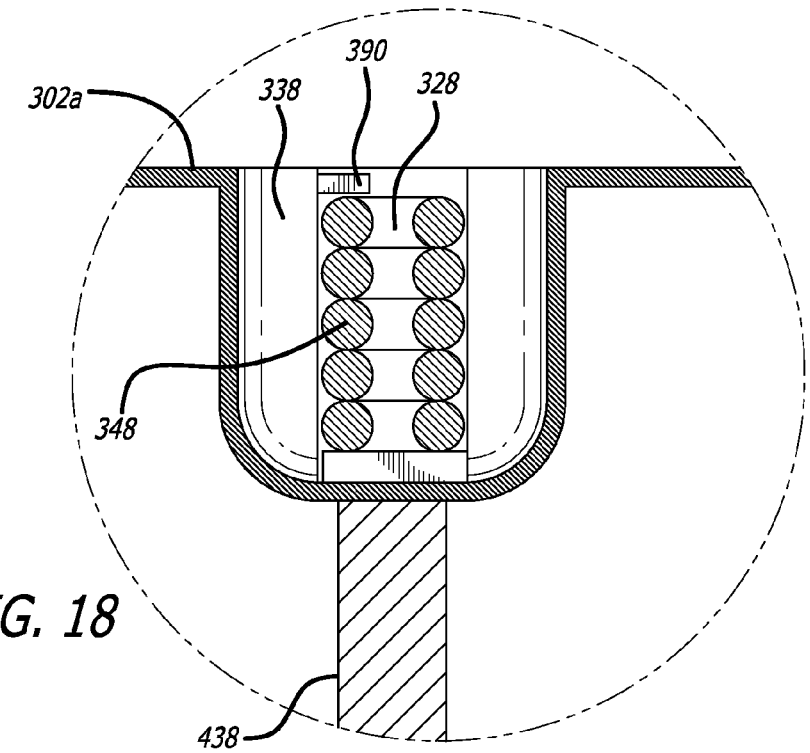
FIG. 18 is a sectional view of a portion of an instrument well taken through plane 18-18 in FIG. 13.
Figure 19:
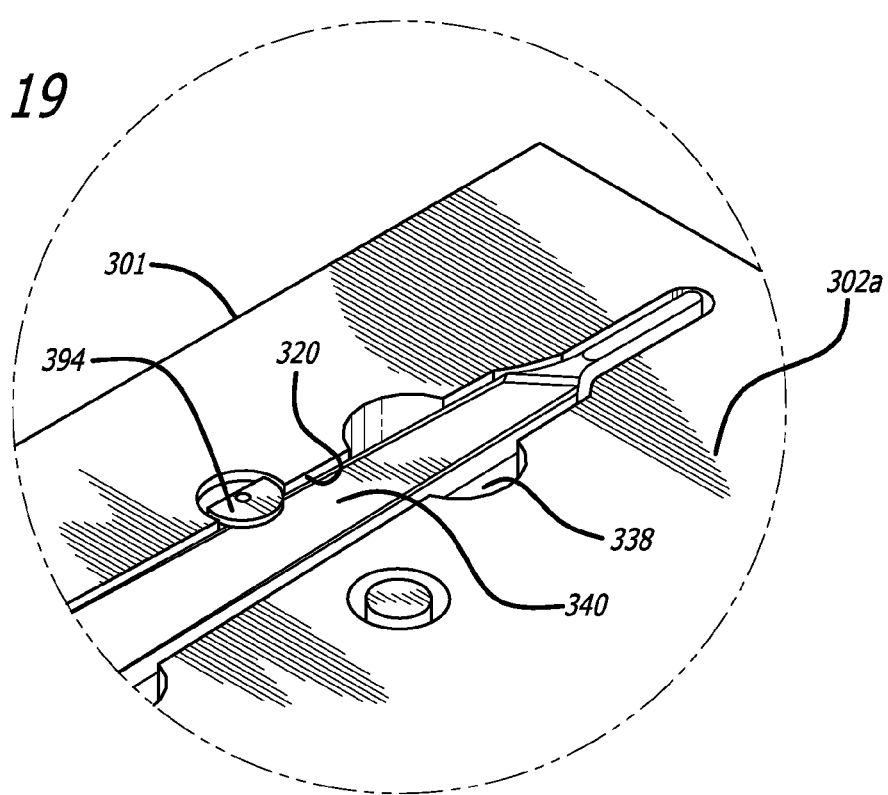
FIGS. 19 and 20 are perspective views of one instrument well at the tray's top surface showing a locking bar in different orientations.
Figure 20:
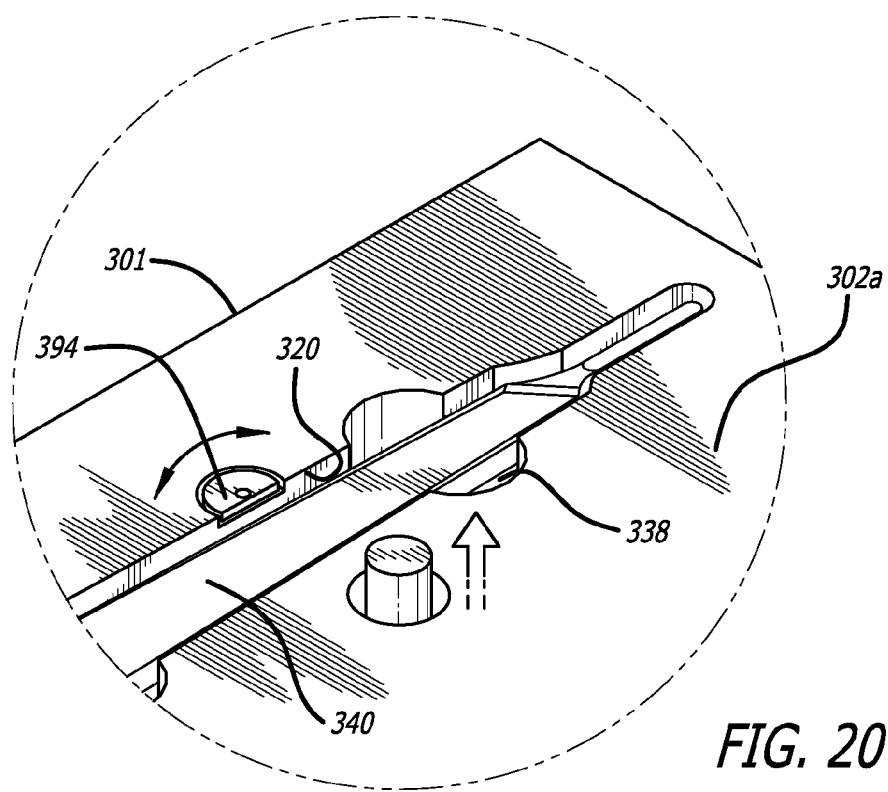

When the locking plate is pivoted to its unlocked orientation, spring 448 raises the instruments 348 and plunger 452. Compare FIGS. 15, 16 and 17. As the plunger rises, the top part of upright portion 454 projects to a position flush or close to flush with surface 302a (FIG. 16) to a position above the surface (FIG. 17). Sidewalls 363 and 365 form instrument well 328, and sidewall 365 has a slot 369 that receives arm 456 of plunger 452. The top of the slot limits the distance the plunger can move upward. Thus, as FIG. 17 shows, the top part of the plunger extends above surface 302a.

As the surgery proceeds, the surgeon and his or her staff use the instruments as necessary until the surgery is finished. Then the instruments are returned to their original, respective instrument well. If the same type and size of surgical instrument fits into two or more instrument wells, the instruments can be returned to any of the proper wells. The top of each plunger only retracts from above the top surface 302a when the correct number of instruments is returned to the proper instrument well. Thus, the top of plunger 452 is pushed below top surface 302a when all five surgical clamps 348 are returned to instrument well 328.

With all clamps returned, the locking plate 390 is pivoted to its lock position. If fewer than five surgical clamps 348 are returned to instrument well 328, the top of plunger 452 remains above top surface 302a. If the person refilling tray 300 after surgery sees any plungers extending about top surfaces 302a or 302b he or she knows that at least one instrument was not returned to the tray. However, if all plungers are retracted, the user knows that all instrument wells are refilled. Thus, all instruments in the tray before the surgery have been returned to tray 300.

The top of each plunger can be colored to contrast with the color of the top surfaces 302*a* and 302*b* to make the visual inspection easier. In addition, the surgeon or staff member can slide a hand over the top surfaces to locate a plunger extending about the top surfaces. If none is felt, the instrument wells are full again and all instruments are back in the tray. If a projecting plunger is felt after all the instruments are reloaded, one knows promptly that an instrument has not been returned. When that occurs, those in the operating room can search for the instrument. Because the search can coincide with returning the instruments to the tray, locating all the instruments used is handled at one time and becomes more efficient.

The description is illustrative, not limiting and is by way of example only. Although this application shows and describes examples, those having ordinary skill in the art will find it apparent that changes, modifications or alterations may be made. Many of the examples involve specific combinations of method, act or system elements, but those acts and elements may be combined in other ways to accomplish the same objectives. Acts, elements and features discussed only in connection with one embodiment are not intended to be excluded from a similar role in other embodiments.

"Plurality" means two or more. A "set" of items may include one or more of such items. The terms "comprising," "including," "carrying," "having," "containing," "involving," and the like in the written description or the claims are open-ended, i.e., each means, "including but not limited to." Only the transitional phrases "consisting of" and "consisting essentially of" are closed or semi-closed transitional phrases with respect to claims. The ordinal terms such as "first," "second," "third," etc., in the claims to modify a claim element do not by themselves connote any priority, precedence, or order of one claim element over another or the temporal order in which acts of a method are performed. Instead, they are used merely as labels to distinguish one claim element having a certain name from another element having a same name (but for use of the ordinal term). Alternatives such as "or" include any combination of the listed items.

I claim:

1. An organizer for holding surgical instruments of particular thicknesses comprising:
    a tray having an upper surface;
    a plurality of indentations in the tray forming instrument wells, at least two of the instrument wells having different shapes, each instrument well having a shape corresponding to the shape of a particular surgical instrument;
    each instrument well having a depth corresponding to the thickness of a stack of surgical instruments of the shape of its instrument well, at least two of the instrument wells having different depths;
    at least one locking plate at the upper surface of the tray and pivotally mounted about an axis generally perpendicular to the upper surface of the tray between a first position covering a portion of at least one instrument well to a second position away from the at least one instrument well, whereby the locking plate in the first position blocks removal and addition of surgical instruments out of or into the at least one instrument well and whereby the locking plate in the second position allowing the removal and addition out of or into the at least one instrument well;
    a plunger mounted in the tray adjacent at least one instrument well, the plunger having an upright portion and a base, the upright portion of the plunger being below the top surface of the tray when the first instrument well contains a predetermined number of stacked surgical instruments, the base of the plunger extending into the first instrument well below all the surgical instruments in the first instrument well; and
    wherein each instrument well has sidewalls and a bottom, the organizer further comprising a tray base spaced from the upper surface of the tray, a pillar mounted on the tray base and extending to the bottom of an instrument well, the pillar having a cavity, the organizer further comprising a plunger mounted in the tray adjacent an instrument well, the plunger having an upright portion having a longitudinal axis generally perpendicular to the upper surface of the tray and a base generally perpendicular to the upright portion, the upright portion of the plunger being below the upper surface of the tray when the instrument well contains its predetermined number of surgical instruments, which are urged together, the base of the plunger extending into the instrument well below all the surgical instruments in the instrument well, a spring mounted in the cavity and being operably connected to the plunger, the spring urging the plunger toward the upper surface of the tray such that the upright portion extends above the upper surface of the tray when the tray contains fewer than the predetermined number of surgical instruments.

2. The organizer of claim 1, wherein the top surface of the tray is generally flat.

3. The organizer of claim 1, wherein the tray is generally rigid.

4. The organizer of claim 1 wherein at least one instrument well has at least one shoulder extending away from the instrument well, the shoulder being positioned a distance below the upper surface of the tray, the locking plate being mounted on the at least one shoulder.

5. The organizer of claim 1 wherein each locking plate is aligned with the upper surface when the instrument well contains the predetermined number of a particular instrument, each locking plate being out of alignment with the upper surface when the instrument well contains fewer or more than the predetermined number of a particular instrument.

6. The organizer of claim 1 wherein the upright portion of the plunger is generally perpendicular to the top surface of the tray, and the base of the plunger is generally perpendicular to the upright portion.

7. An organizer for holding surgical instruments of particular thicknesses comprising:
    a tray having an upper surface;
    a plurality of indentations in the tray forming instrument wells, at least two of the instrument wells having different shapes, each instrument well having a shape corresponding to the shape of a particular surgical instrument;
    each instrument well having a depth corresponding to the thickness of a stack of surgical instruments of the shape of its instrument well, at least two of the instrument wells having different depths;
    at least one locking plate at the upper surface of the tray and pivotally mounted about an axis generally perpendicular to the upper surface of the tray between a first position covering a portion of at least one instrument well to a second position away from the at least one instrument well, whereby the locking plate in the first position blocks removal and addition of surgical instruments out of or into the at least one instrument well and whereby the locking plate in the second position allowing the removal and addition out of or into the at least one instrument well;

a plunger mounted in the tray adjacent at least one instrument well, the plunger having an upright portion and a base, the upright portion of the plunger being below the top surface of the tray when the first instrument well contains a predetermined number of stacked surgical instruments, the base of the plunger extending into the first instrument well below all the surgical instruments in the first instrument well;

a spring mounted in the tray operably connected to the plunger, the spring urging the plunger toward the top surface of the tray such that the upright portion extends above the top surface of the tray when the tray contains fewer than the predetermined number of surgical instruments; and wherein each instrument well has sidewalls and a bottom, the organizer further comprising a tray base spaced from the top surface of the tray, a pillar mounted on the tray base and extending to the bottom of an instrument well, the pillar having a cavity, the organizer further comprising a plunger mounted in the tray adjacent an instrument well, the plunger having an upright portion having a longitudinal axis generally perpendicular to the top surface of the tray and a base generally perpendicular to the upright portion, the upright portion of the plunger being below the top surface of the tray when the first instrument well contains its predetermined number of surgical instruments, which are urged together, the base of the plunger extending into the first instrument well below all the surgical instruments in the first instrument well, a spring mounted in the cavity and being operably connected to the plunger, the spring urging the plunger toward the top surface of the tray such that the upright portion extends above the top surface of the tray when the tray contains fewer than the predetermined number of surgical instruments.

8. The organizer of claim 7, wherein the upper surface of the tray is generally flat.

9. The organizer of claim 7, wherein the tray is generally rigid.

10. The organizer of claim 7 wherein the first instrument well has at least one shoulder extending away from the first instrument well, the shoulder being positioned a distance below the upper surface of the tray, the locking plate being mounted on the at least one shoulder.

11. The organizer of claim 7 wherein the locking plate is aligned with the upper surface when the first instrument well contains the predetermined number of a particular instrument, the locking plate being out of alignment with the upper surface when the first instrument well contains fewer or more than the predetermined number of a particular instrument.

12. The organizer of claim 7 wherein the upright portion of the plunger is generally perpendicular to the top surface of the tray, and the base of the plunger is generally perpendicular to the upright portion.

* * * * *